United States Patent
Nagata et al.

(10) Patent No.: US 9,968,492 B2
(45) Date of Patent: May 15, 2018

(54) METHOD OF AND APPARATUS FOR MANUFACTURING BLOOMED FIBER MATERIAL

(71) Applicant: DAICEL CORPORATION, Osaka-shi, Osaka (JP)

(72) Inventors: Shingo Nagata, Himeji (JP); Masato Shigematsu, Himeji (JP); Toshiyuki Morioka, Himeji (JP)

(73) Assignee: DAICEL CORPORATION, Osaka-shi (JP)

( * ) Notice: Subject to any disclaimer, the term of this patent is extended or adjusted under 35 U.S.C. 154(b) by 123 days.

(21) Appl. No.: 15/110,353

(22) PCT Filed: Dec. 26, 2014

(86) PCT No.: PCT/JP2014/006509
§ 371 (c)(1),
(2) Date: Jul. 7, 2016

(87) PCT Pub. No.: WO2015/104788
PCT Pub. Date: Jul. 16, 2015

(65) Prior Publication Data
US 2016/0333507 A1    Nov. 17, 2016

(30) Foreign Application Priority Data
Jan. 8, 2014 (JP) .................. 2014-001579

(51) Int. Cl.
*D02J 1/18* (2006.01)
*A61F 13/15* (2006.01)
*D02G 1/16* (2006.01)

(52) U.S. Cl.
CPC .. *A61F 13/15723* (2013.01); *A61F 13/15666* (2013.01); *D02G 1/161* (2013.01); *D02J 1/18* (2013.01)

(58) Field of Classification Search
CPC ........ D02J 1/18; D02J 1/02; D02J 1/12; D02J 1/20; D02J 11/00; D02G 1/16;
(Continued)

(56) References Cited

U.S. PATENT DOCUMENTS 2,794,239 A * 6/1957 Crawford ............... A24D 3/022
131/343
3,016,581 A * 1/1962 Smith .................. A24D 3/0204
156/181
(Continued)

FOREIGN PATENT DOCUMENTS

CH      469111 A       2/1969
JP      45-16910       6/1970
(Continued)

OTHER PUBLICATIONS

International Search Report, issued in PCT/JP2014/006509, dated Apr. 7, 2015.
(Continued)

*Primary Examiner* — Amy Vanatta
(74) *Attorney, Agent, or Firm* — Birch, Stewart, Kolasch & Birch, LLP (57) ABSTRACT

A bloomed fiber material (bloomed tow) is manufactured through a process including: spreading a crimped tow in its width direction by a preliminary blooming device; performing primary blooming to bloom the tow by a primary blooming device; dividing the tow into at least two divided tows by a dividing device; cutting a parting between the divided tows by a cutting device; and performing secondary blooming to bloom the divided tows by a secondary blooming device.

20 Claims, 5 Drawing Sheets

(58) Field of Classification Search
CPC ............ D02G 1/161; D02G 1/20; D02G 1/00; D01D 11/02; A61F 13/15723; A61F 13/15666; A61F 13/15577; A61F 13/15707
USPC .................................................. 28/282, 283
See application file for complete search history.

(56) References Cited

U.S. PATENT DOCUMENTS

| | | | | |
|---|---|---|---|---|
| 3,079,663 | A * | 3/1963 | Dyer | A24D 3/0233 156/178 |
| 3,156,016 | A * | 11/1964 | Dunlap | D02J 1/18 156/166 |
| 3,328,850 | A * | 7/1967 | Watson | D02G 3/06 19/65 T |
| 3,796,035 | A * | 3/1974 | Watson | D02G 1/18 28/283 |
| 3,910,166 | A | 10/1975 | Sexstone | |
| 3,960,645 | A * | 6/1976 | Brackmann | A24D 3/0204 156/180 |
| 4,435,239 | A * | 3/1984 | Harris | D01D 11/02 156/180 |
| 4,497,098 | A | 2/1985 | Lay et al. | |
| 2006/0053593 | A1 | 3/2006 | Gombash, Jr. | |

FOREIGN PATENT DOCUMENTS

| | | |
|---|---|---|
| JP | 48-64534 U | 8/1973 |
| JP | 56-4724 A | 1/1981 |
| JP | 57-25434 A | 2/1982 |
| JP | 2007-21181 A | 2/2007 |

OTHER PUBLICATIONS

English Translation of International Preliminary Report on Patentability, issued in PCT/JP2014/006509, dated Jul. 12, 2016.

* cited by examiner

METHOD OF AND APPARATUS FOR MANUFACTURING BLOOMED FIBER MATERIAL

TECHNICAL FIELD

The present invention relates to a method of and an apparatus for manufacturing a bloomed or opened fiber material for use in a disposable diaper or the like.

BACKGROUND ART

Conventionally, a composite of a tow that has been bloomed or opened (hereinafter, a "bloomed tow" or "bloomed fiber material") and a polymer absorbent, the composite being wrapped up in paper, has been used as an absorber for use in a disposable diaper or the like. The bloomed tow is obtained by blooming or opening a single original tow with use of blooming rollers and blooming jets, and is usually single-layered. In a case where a layered body of such bloomed tows is required, first, a plurality of single-layered bloomed tows are fabricated, and then the plurality of single-layered bloomed tows are stacked together to be a multi-layered body. In this manner, a layered body of bloomed tows is manufactured. When manufacturing such a layered body of bloomed tows, a plurality of tow bales and blooming equipment for blooming the tows are necessary. Thus, there have been problems in terms of costs and installation space.

In order to overcome the above problems, Patent Literature 1 proposes a method of manufacturing an absorber by using two layers of bloomed tows that are fabricated from a single original tow. The manufacturing method of Patent Literature 1 includes: blooming an original tow by using blooming devices (banding jets and blooming rollers) in a state where the tow is extended in its longitudinal direction; cutting the bloomed tow in its longitudinal direction into two bloomed tows by using an anvil roller and a roll slitter; and reducing the tensile strength of each of the bloomed tows by using a vacuum conveyor, such that the bloomed tows are crimped.

CITATION LIST

Patent Literature

PTL 1: Japanese Laid-Open Patent Application Publication No. 2007-21181

SUMMARY OF INVENTION

Technical Problem

When the bloomed tow is cut in its longitudinal direction as described in Patent Literature 1, cut ends of tow filaments protrude from a cut surface of the bloomed tow. The tow filaments protruding from the cut surface of the bloomed tow may cause manufacturing troubles, for example, getting entangled with a drive shaft during the manufacturing. Moreover, tow filaments that have been cut short may fall or become lifted from the cut surface of the bloomed tow, causing deformation of the cut surface line. This may cause degradation in the quality of the bloomed tow.

The present invention has been made in view of the above. The present invention is directed to a method of and an apparatus for manufacturing a plurality of bloomed fiber materials (bloomed tows) from a single original tow, and an objective of the present invention is to improve the quality of the manufactured bloomed fiber materials.

Solution to Problem

A method of manufacturing a bloomed fiber material according to the present invention includes: spreading a crimped tow in a width direction of the tow; performing primary blooming to bloom the tow that has been spread in the width direction; dividing the tow that has undergone the primary blooming into at least two divided tows; cutting a parting between the divided tows; and performing secondary blooming to bloom the divided tows.

An apparatus for manufacturing a bloomed fiber material according to the present invention includes: a preliminary blooming device configured to spread a crimped tow in a width direction of the tow; a primary blooming device configured to perform primary blooming to bloom the tow that has been spread in the width direction; a dividing device configured to divide the tow that has undergone the primary blooming into at least two divided tows; a cutting device configured to cut a parting between the divided tows; and a secondary blooming device configured to perform secondary blooming to bloom the divided tows.

According to the above bloomed fiber material manufacturing method and apparatus, the tow is divided into a plurality of divided tows, and then the parting between the divided tows is cut. Therefore, the amount of filaments that are cut is reduced compared to a case where the tow is cut without being divided as described in Patent Literature 1. In other words, the amount of filaments that have been cut short, which may cause quality degradation of the bloomed fiber material, can be reduced in the bloomed fiber material. Moreover, cut ends of the filaments, which result from the cutting, can be buried inside the bloomed fiber material by performing the blooming (secondary blooming). As a result, the cut ends of the filaments are less likely to protrude from the bloomed fiber material. Furthermore, after the tow has been divided into the divided tows, the divided tows are bloomed (secondary blooming). Accordingly, in each manufactured bloomed fiber material, the filaments are well intertwined with one another. As a result, the shape of the bloomed fiber material is not easily deformed. At least from the above-described points, the bloomed fiber materials manufactured by the above bloomed fiber material manufacturing method and apparatus have higher quality than a plurality of bloomed tows that are obtained by blooming a single tow and then cutting the bloomed tow as described in Patent Literature 1.

Advantageous Effects of Invention

The present invention makes it possible to improve the quality of manufactured bloomed fiber materials.

DESCRIPTION OF EMBODIMENTS

Figure 1:
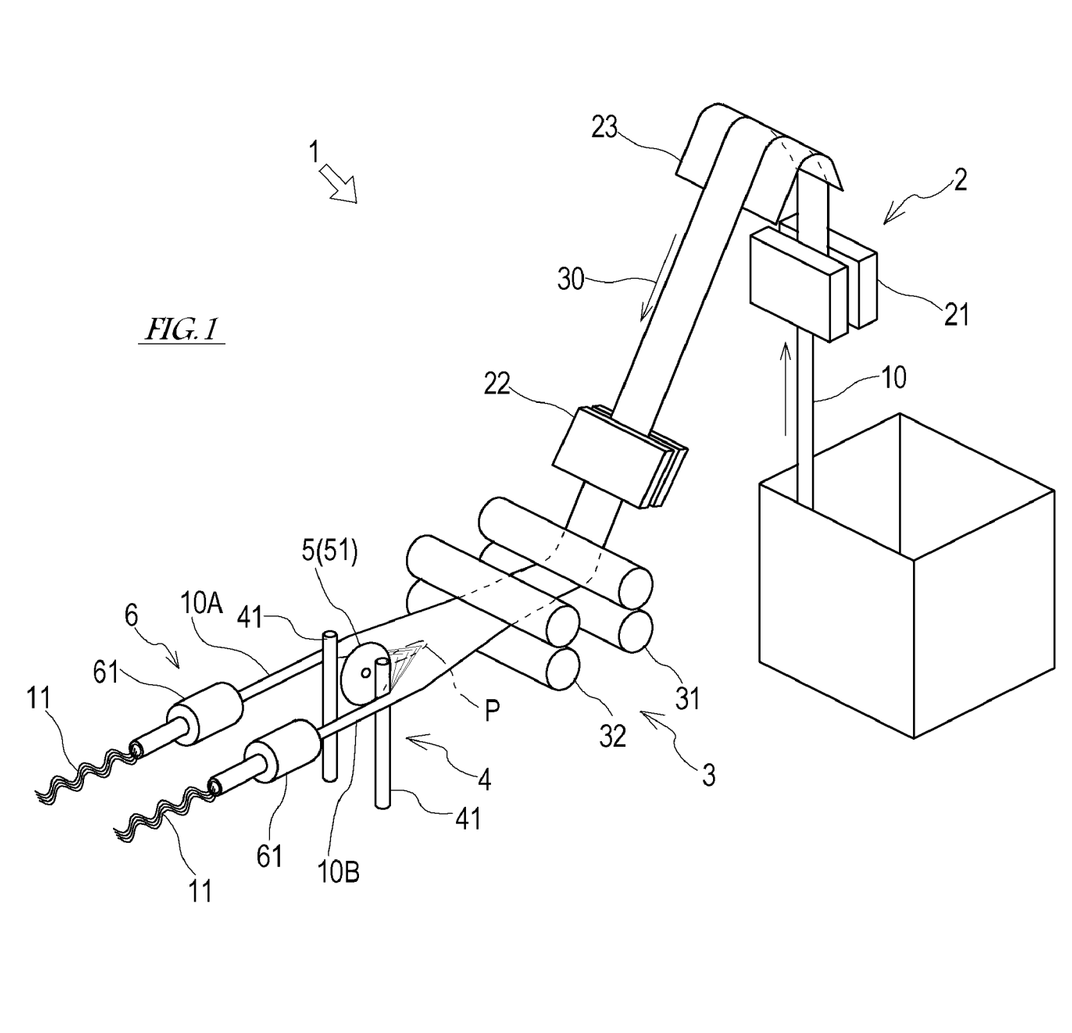
FIG. 1 shows an overall configuration of a bloomed fiber material manufacturing apparatus according to one embodiment of the present invention.
Figure 2:
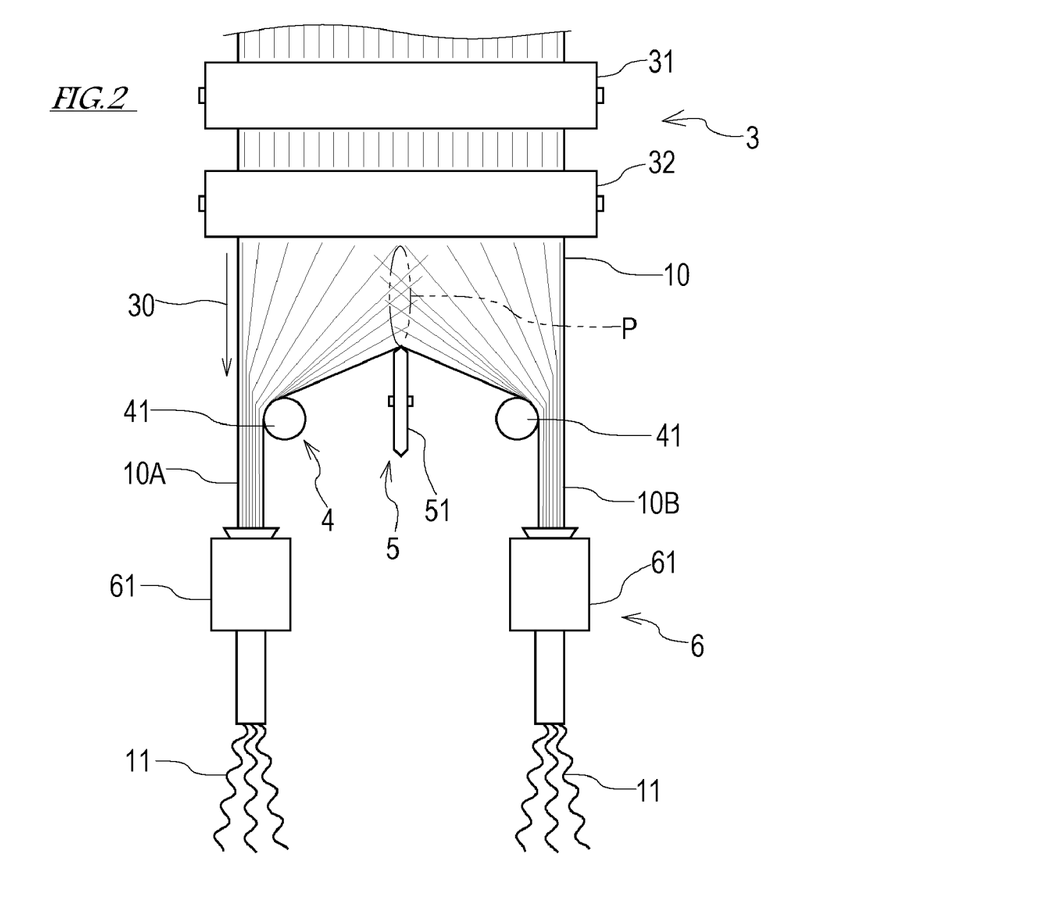
FIG. 2 is a plan view showing a part of the bloomed fiber material manufacturing apparatus, which part is positioned following a primary blooming device.
Figure 3:
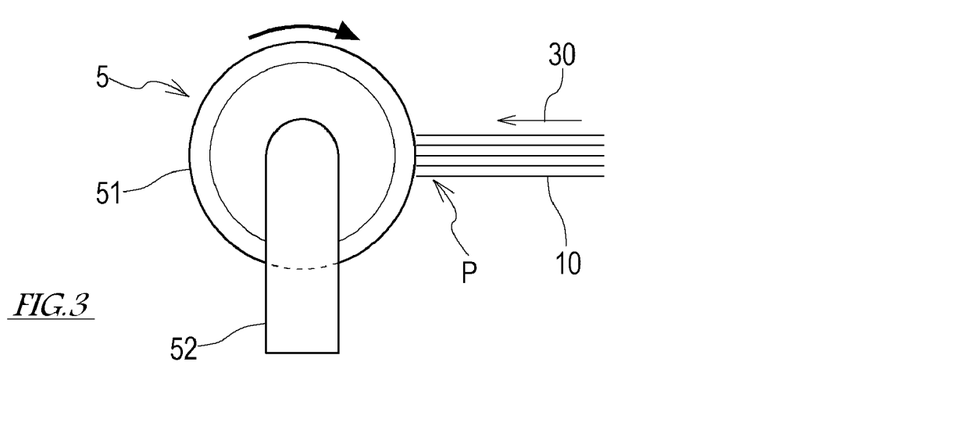
FIG. 3 is a side view showing a cutting device.

Hereinafter, one embodiment of the present invention is described with reference to the drawings. FIG. 1 shows an overall configuration of a bloomed fiber material manufacturing apparatus 1 according to one embodiment of the present invention. FIG. 2 is a plan view showing a part of the bloomed fiber material manufacturing apparatus 1, which part is positioned following a primary blooming device 3. FIG. 3 is a side view showing a cutting device 5.

As shown in FIGS. 1 to 3, the bloomed fiber material manufacturing apparatus 1 according to the present embodiment is an apparatus for manufacturing a plurality of bloomed tows 11 (bloomed fiber materials) from a single tow bale (original fibers from which a tow 10 is obtained). The plurality of manufactured bloomed tows 11 may be layered together to be used as a layered body of bloomed tows, or may be used as a plurality of bloomed tows arranged parallel to each other. For example, the tow 10 may be, but is not limited to, a cellulose acetate tow.

A feeding path 30 for feeding the tow 10 is formed in the bloomed fiber material manufacturing apparatus 1. The manufacturing apparatus 1 includes a preliminary blooming device 2, the primary blooming device 3, a dividing device 4, a cutting device 5, and a secondary blooming device 6, which are sequentially arranged in this order along the feeding path 30 in the tow feeding direction. Hereinafter, each of the components of the bloomed fiber material manufacturing apparatus 1 is described in detail.

The preliminary blooming device 2 is means for preliminarily blooming the tow 10, which is drawn from the tow bale and is in a crimped state, and forming the tow 10 into a tow band. In the present embodiment, two banding jets 21 and 22 are used as the preliminary blooming device 2. The banding jet 21 is disposed on the feeding path 30 between the tow bale and a guide 23. The banding jet 22 is disposed on the feeding path 30 between the guide 23 and the primary blooming device 3. The banding jets 21 and 22 jet out compressed air onto the surface of the tow 10 when the tow 10 passes them through, thereby separating the filaments of the tow 10 from one another. Owing to the function of the banding jets 21 and 22, the width of the tow 10 is expanded, and thus the tow 10 is formed into a tow band.

The primary blooming device 3 is means for blooming (primary blooming) the tow 10 that has undergone the preliminary blooming by the preliminary blooming device 2. In the present embodiment, two pairs of blooming rollers 31 and 32 are used as the primary blooming device 3. The two pairs of blooming rollers 31 and 32 are disposed on the feeding path 30, such that the two pairs of rollers are away from each other in the feeding direction of the tow 10 by a predetermined space. The pair of blooming rollers 32, which is positioned following the pair of blooming rollers 31, is driven to rotate at a speed slightly higher than the rotation speed of the pair of blooming rollers 31. The primary blooming device 3 with this configuration stretches and loosens the tow 10 between the two pairs of blooming rollers 31 and 32. As a result, individual filaments of the tow 10 are separated from one another.

The dividing device 4 is means for dividing the single tow 10 that has undergone the primary blooming by the primary blooming device 3 into at least two tows 10A and 10B (hereinafter, "divided tows 10A and 10B"). A parting P extending in the longitudinal direction of the tow 10 is formed between the divided tows 10A and 10B. In the present embodiment, two guide bars 41 (guide members) are used as the dividing device 4 for forming the two divided tows 10A and 10B from the single tow 10. The cutting device 5 is means for cutting the tow 10 along the formed parting P. In the present embodiment, a disc cutter 51 driven by a driver 52 (FIG. 3) to rotate is used as the cutting device 5.

The two guide bars 41 are disposed away from each other in the width direction of the tow 10 such that, on the feeding path 30, the guide bars 41 are positioned inside both ends of the moving tow 10 in its width direction. The two guide bars 41 divide the single tow 10 in its width direction into the two divided tows 10A and 10B. In addition, the two guide bars 41 guide the movement of the divided tows 10A and 10B, such that the divided tows 10A and 10B are separated apart from each other in the width direction of the tow 10. Almost all of the filaments of the tow 10 move into either the divided tow 10A or the divided tow 10B without being cut.

At the parting P formed between the two divided tows 10A and 10B separated apart from each other, filaments of the one divided tow 10A and filaments of the other divided tow 10B cross each other. Each of these crossing filaments, as moving forward on the feeding path 30, finally entirely moves into the flow of one of the two divided tows 10A and 10B. Accordingly, in the parting P, the amount of filaments decreases as the filaments move forward on the feeding path 30.

The disc cutter 51 is disposed in a part of the parting P, which part faces the secondary blooming device and in which part the amount of filaments is small, or is disposed at a position following the parting P, at which position no filament is to be present. Accordingly, only the filaments that have not been divided by the dividing device 4 are cut by the disc cutter 51. Therefore, the tow 10 can be sufficiently cut by the disc cutter 51 without requiring the use of an anvil for the disc cutter 51, such as an anvil roller. It should be noted that, as described in Patent Literature 1, in the case of cutting a tow by using an anvil roller and a roll slitter, since the roll slitter is pressed against the anvil roller, the blade of the roll slitter tends to wear quickly. On the other hand, in the present embodiment, since the blade of the disc cutter 51 comes into contact only with the filaments, the blade of the disc cutter 51 wears less than in the case of adopting the configuration of Patent Literature 1. This makes it possible to reduce the frequency of the replacement of the blade of the disc cutter 51.

The distance by which the two guide bars 41 are spaced apart from each other in the width direction of the tow 10 is not particularly limited. That is, the distance between the two guide bars 41 may be less than, equal to, or greater than the width of the tow 10. Also, the installation positions of the two guide bars 41 on the feeding path 30 are not particularly limited. That is, on the feeding path 30, the two guide bars 41 may be disposed preceding, following, or at the same position as, the disc cutter 51. However, the installation positions of the guide bars 41 on the feeding path 30 are set such that the closest part of the parting P to the primary blooming device, the parting P being formed in the tow 10 by the two guide bars 41, is positioned preceding the disc cutter 51 on the feeding path 30. In the present embodiment, the disc cutter 51 is disposed between the two guide bars 41, which are spaced apart from each other.

The secondary blooming device 6 is means for blooming (secondary blooming) each of the divided tows 10A and 10B, and reducing the tensile strength of each of the divided tows 10A and 10B. In the present embodiment, blooming jets 61 are used as the secondary blooming device 6. The divided tows 10A and 10B are drawn into the blooming jets 61, and the blooming jets 61 are configured to jet out the divided tows 10A and 10B from their nozzles together with compressed air. The blooming jets 61 perform: separating the filaments of each of the divided tows 10A and 10B from one another; forming each of the divided tows 10A and 10B into an intended shape (having an intended width and volume); and reducing the tensile strength of each of the divided tows 10A and 10B. As a result, the divided tows 10A and 10B, which have undergone the secondary blooming by the blooming jets 61, become bloomed tows 11, each of which has an intended shape.

The shape of the nozzles of the blooming jets 61 is not particularly limited. However, desirably, the nozzles of the blooming jets 61 are cylindrical nozzles. If the nozzles of the blooming jets 61 are cylindrical, the cut surfaces of the divided tows 10A and 10B and the cut ends of the filaments, which result from the cutting, tend to be buried inside the bloomed tows 11. As a result, the protrusion of the cut ends of the filaments from the bloomed tows 11 can be eliminated or reduced. This makes it possible to further improve the quality of the bloomed tows 11.

In the bloomed fiber material manufacturing apparatus 1 with the above-described configuration, the preliminary blooming device 2 and the primary blooming device 3 are provided for the single tow 10, and the secondary blooming device 6 is provided for the two divided tows 10A and 10B. In other words, except the secondary blooming device 6, it will suffice if the bloomed fiber material manufacturing apparatus 1 is provided with processing equipment intended for the single tow 10. Therefore, compared to conventional art in which two tow bales and blooming equipment for blooming the tows are installed for manufacturing two bloomed tows, the bloomed fiber material manufacturing apparatus 1 according to the present embodiment makes it possible to reduce the initial cost and the running cost. Moreover, since the manufacturing apparatus 1 is made compact, its installation space can be reduced.

Figure 4:
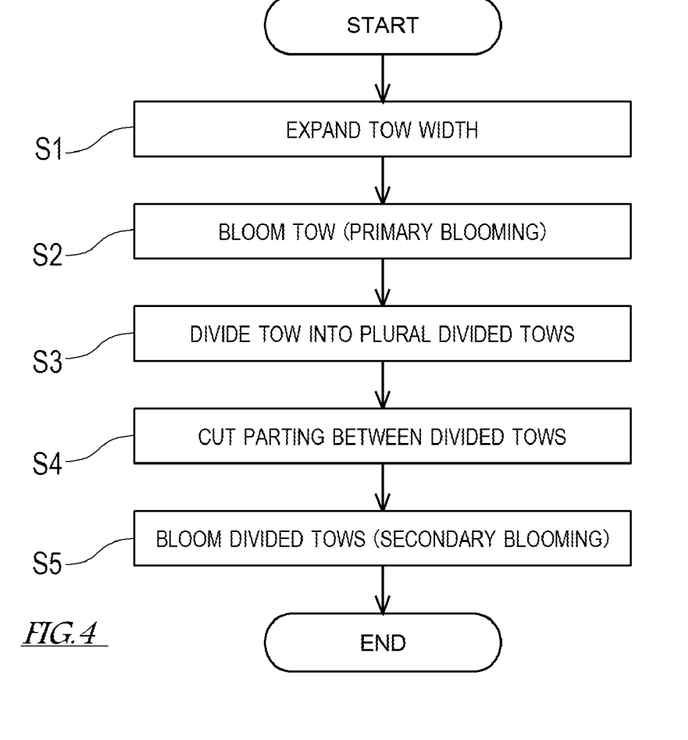
FIG. 4 is a flowchart illustrating a bloomed fiber material manufacturing method.

Next, a method of manufacturing a bloomed fiber material by using the bloomed fiber material manufacturing apparatus 1 with the above-described configuration is described. FIG. 4 is a flowchart illustrating the bloomed fiber material manufacturing method.

As shown in FIG. 4, a tow 10 that is drawn from a tow bale and extended in its longitudinal direction undergoes the following steps. First, the width of the tow 10 is expanded by the preliminary blooming device 2 (step S1). Then, the resulting band-shaped tow 10 undergoes the primary blooming by the primary blooming device 3 (step S2). In the primary blooming, individual filaments of the tow 10 are separated from one another by the pairs of blooming rollers 31 and 32.

Next, the tow 10, which has undergone the primary blooming, is divided by the dividing device 4 into a plurality of (two) divided tows 10A and 10B, and also, the divided tows 10A and 10B are separated apart from each other in the width direction (step S3). Further, the filaments in the parting P formed between the two divided tows 10A and 10B separated apart from each other are cut by the cutting device 5 (step S4). Finally, the divided tows 10A and 10B undergo the secondary blooming by the secondary blooming device 6 (step S5). In the secondary blooming, each of the divided tows 10A and 10B is bloomed and formed into an intended shape (having an intended width and volume), and also, the tensile strength of each of the divided tows 10A and 10B is reduced, such that the divided tows 10A and 10B are crimped.

In accordance with the above-described series of steps, two bloomed tows 11 are manufactured from a single original tow. The manufactured bloomed tows 11 are fed to the next process by a conveyor that is not shown. It should be noted that, unlike Patent Literature 1, it is not necessary for the manufacturing apparatus 1 to include a vacuum conveyor for reducing the tensile strength of each of the bloomed tows, because the tensile strength of each of the tows 10A and 10B is reduced by the blooming jets 61 in the above secondary blooming.

In the above-described manufacturing method, the tow 10 is divided by the dividing device 4 into a plurality of divided tows, and then the parting P between the divided tows is cut by the cutting device 5. Therefore, the amount of filaments that are cut is significantly reduced compared to a case where the tow 10 is cut without being divided as in Patent Literature 1. In other words, the amount of filaments that have been cut short, which may cause quality degradation, can be reduced in the bloomed tows.

In the above-described manufacturing method, after the tow 10 has been divided into the divided tows 10A and 10B, the divided tows 10A and 10B are bloomed by the blooming jets 61 (secondary blooming). Accordingly, in each manufactured bloomed tow 11, the filaments are well intertwined with one another. As a result, the shape of the bloomed tow 11 is not easily deformed. Also, each manufactured bloomed tow 11 is excellent in terms of bulkiness and fluffiness. Moreover, the cut surfaces of the divided tows 10A and 10B and the cut ends of the filaments, which result from the cutting, are buried inside the bloomed tows 11 owing to the secondary blooming being performed. Therefore, the cut ends of the filaments do not protrude from the bloomed tows.

As described above, the bloomed fiber material manufacturing method and the bloomed fiber material manufacturing apparatus 1 according to the present embodiment make it possible to manufacture bloomed tows with higher quality than a plurality of bloomed tows that are obtained by blooming a single tow and then cutting the bloomed tow as described in Patent Literature 1.

Evaluation Experiment 1

Next, experiment results are shown. The experiment was conducted to evaluate bloomed tows that were manufactured with the above-described manufacturing method by using the bloomed fiber material manufacturing apparatus 1 according to the present embodiment. In the evaluation experiment 1, structured bodies were manufactured (a structured body according to Working Example 1 and structured bodies according to Comparative Examples 1 and 2), each of which was manufactured by sandwiching an absorbent between two bloomed tows that were vertically stacked one on top of the other. Then, the properties of these structured bodies were compared.

Table 1 shown below indicates manufacturing conditions of the bloomed tows included in the structured body according to Working Example 1 and the structured bodies according to Comparative Examples 1 and 2. The structured body according to Working Example 1 was obtained in the following manner: manufacturing two bloomed tows from a single tow in the above-described manner by using the bloomed fiber material manufacturing apparatus 1 according to the present embodiment; and sandwiching an absorbent (SAP: Superabsorbent polymer) between the two bloomed tows, which were vertically stacked one on top of the other. The structured body according to Comparative Example 1 was obtained in the following manner: blooming a single tow with banding jets and pairs of blooming rollers and cutting the bloomed tow in its longitudinal direction by using an anvil roller and a roll slitter as described in Patent Literature 1, thereby manufacturing two bloomed tows; and sandwiching the absorbent between the two bloomed tows, which were vertically stacked one on top of the other. The structured body according to Comparative Example 2 was obtained in the following manner: manufacturing two bloomed tows by blooming each of two tows with pairs of blooming rollers and blooming jets; and sandwiching the absorbent between the two bloomed tows, which were vertically stacked one on top of the other.

TABLE 1

| Manufacturing Conditions of Bloomed Tows | Working Example 1 | Comparative Example 1 | Comparative Example 2 |
| --- | --- | --- | --- |
| Number of Tows Used | 1 | 1 | 2 |
| TD of Tow Used | High | High | Low |
| Means for Blooming | Pairs of blooming rollers and blooming jets | Pairs of blooming rollers | Pairs of blooming rollers and blooming jets |
| Division before Cutting | Divided | Not divided | Not divided |
| Means for Cutting | Disc cutter | Roll slitter and anvil roller | None |
| Means for Feeding | Conveyor | Vacuum conveyor | Conveyor |

Table 2 shown below indicates results of evaluation of the properties of the structured body according to Working Example 1 and the structured bodies according to Comparative Examples 1 and 2. The properties of the structured bodies were evaluated for the following items: weight stability; width stability; bulkiness; compression restorability; shape maintainability; thickness uniformity; cut surface shape; and absorbent retention.

TABLE 2

| Properties of Structured body | Working Example 1 | Comparative Example 1 | Comparative Example 2 | Notes |
| --- | --- | --- | --- | --- |
| Weight Stability | Good | Good | Good | Variation ($\sigma$) in the average value of the weight measured at 10 points every 30 cm on each bloomed tow (the measurement was conducted under the same conditions for the same tows in a non-divided state with the ratio adjusted to 1.8 g/30 cm).<br>Good: $\sigma = 2.6$ or less (same level as existing tow products)<br>Not so good: $\sigma = 2.7$ to 2.9<br>Poor: $\sigma = 3.0$ or more |
| Width Stability | Good | Good | Good | Variation ($\sigma$) in the average value of the width measured at 20 points every 15 cm on each bloomed tow (the measurement was conducted under the same conditions for the same tows in a non-divided state with the width adjusted to 65 mm).<br>Good: $\sigma = 0.04$ or less (same level as existing tow products)<br>Not so good: $\sigma = 0.05$ to 0.09<br>Poor: $\sigma = 0.10$ or more |
| Bulkiness (Feeling Evaluation) | Good (2.1 mm) | Poor (0.7 mm) | Good (2.1 mm) | Good: Bloomed tow is sufficiently bulky in thickness direction.<br>Not so good: Tow is bloomed, but insufficient in terms of fluffiness.<br>Poor: Fibers are not bulky and feel thin |
| Compression Restorability (Feeling Evaluation) | Good (175%) | Poor (175%) | Good (180%) | Good: Resilient to restore original thickness when pushed.<br>Not so good: Soft, but does not restore original thickness.<br>Poor: Flattened when load is applied. |
| Shape Maintainability (Feeling Evaluation) | Good | Poor | Good | Good: Not deformed even when touched firmly.<br>Not so good: Not deformed only when touched lightly.<br>Poor: Deformed even when touched lightly. |
| Thickness Uniformity (Visual Confirmation) | Good | Not so good | Good | Good: Almost no visible line (thin portion or crack).<br>Not so good: Line is visible, but it does not affect the feel of touch.<br>Poor: Large line nearly causing crack, and feels clearly thin when touching it. |
| Cut Surface Condition (Visual Confirmation) | Good | Poor | Good | Good: No visible cut in fiber.<br>Not so good: Some visible cuts in fiber, but they do not affect the shape of bloomed fiber material.<br>Poor: Cut surface is clearly visible. |

TABLE 2-continued

| Properties of Structured body | Working Example 1 | Comparative Example 1 | Comparative Example 2 | Notes |
|---|---|---|---|---|
| Absorbent Retention | Good | Poor | Good | The degree of SAP permeation when constant amount of SAP was spread onto each bloomed tow from above and constant vibration was applied to the tow. |

It is understood from Table 2 that the structured body according to Working Example 1 has better properties than the structured body according to Comparative Example 1, and the structured body according to Working Example 1 has substantially equivalent properties to those of the structured body according to Comparative Example 2. It should be noted that in order to manufacture the bloomed tows that serve as the materials of the structured body according to Comparative Example 2, two tow bales and manufacturing equipment for manufacturing the bloomed tows are necessary. On the other hand, in the case of manufacturing the bloomed tows that serve as the materials of the structured body according to Working Example 1, except the secondary blooming device 6, it will suffice if the bloomed fiber material manufacturing apparatus 1 is provided with a single tow bale and blooming equipment for blooming the single tow. Therefore, the structured body according to Working Example 1 is more advantageous in terms of costs and installation space of the manufacturing equipment as compared to the structured body according to Comparative Example 2. Moreover, the TD (total denier) of the tow used to manufacture the bloomed tows that serve as the materials of the structured body according to Working Example 1 is higher than the TD of the tows used to manufacture the bloomed tows that serve as the materials of the structured body according to Comparative Example 2. Therefore, the productivity of the bloomed tows is higher in the case of the structured body according to Working Example 1

Evaluation Experiment 2

In Evaluation Experiment 2, bloomed tows each having an extremely small basis weight (weight per square meter) were manufactured (a bloomed tow according to Working Example 2 and a bloomed tow according to Comparative Example 3), and the properties of these bloomed tows were compared.

Table 3 shown below indicates the manufacturing conditions of the bloomed tow according to Working Example 2 and the bloomed tow according to Comparative Example 3. The bloomed tow according to Working Example 2 was one of two bloomed tows that had been manufactured from a single tow in the above-described manner by using the bloomed fiber material manufacturing apparatus 1 according to the present embodiment. The bloomed tow according to Comparative Example 3 was obtained by blooming a single tow with pairs of blooming rollers and blooming jets.

TABLE 3

| Manufacturing Conditions of Bloomed Tow | Working Example 2 | Comparative Example 3 |
|---|---|---|
| TD of Tow Used | 25,000 divided into substantially two halves (12,500 per tow) | 25,000 |
| Means for Blooming | Pairs of blooming rollers and blooming jets | Pairs of blooming rollers and blooming jets |
| Division before Cutting | Divided | Not divided |
| Means for Cutting | Disc cutter | None |

Table 4 shown below indicates results of evaluation of the properties of the bloomed tow according to Working Example 2 and the bloomed tow according to Comparative Examples 3. The properties of the bloomed tows were evaluated for the following items: basis weight; thickness; tow weight stability; tow width stability; shape maintainability; thickness uniformity; and cut surface shape.

TABLE 4

| Properties of Bloomed Tow | Working Example 2 | Comparative Example 3 | Notes |
|---|---|---|---|
| Basis Weight | 33.5 g/m$^2$ | 67 g/m$^2$ | |
| Thickness | 4 mm | 7 mm | |
| Tow Weight Stability | Good | Good | Variation ($\sigma$) in the average value of the weight measured at 10 points every 30 cm on each bloomed tow (the measurement was conducted under the same conditions for the same tows in a non-divided state with the ratio adjusted to 1.8 g/30 cm). Good: $\sigma = 2.6$ or less (same level as existing tow products) Not so good: $\sigma = 2.7$ to 2.9 Poor: $\sigma = 3.0$ or more |
| Tow Width Stability | Good | Good | Variation ($\sigma$) in the average value of the width measured at 20 points every 15 cm on each bloomed tow (the measurement was conducted under the same conditions for the same tows in a non-divided state with the width adjusted to 65 mm). Good: $\sigma = 0.04$ or less (same level as existing tow products) Not so good: $\sigma = 0.05$ to 0.09 Poor: $\sigma = 0.10$ or more |

TABLE 4-continued

| Properties of Bloomed Tow | Working Example 2 | Comparative Example 3 | Notes |
|---|---|---|---|
| Shape Maintainability (Feeling Evaluation) | Good | Good | Good: Not deformed even when touched firmly. Not so good: Not deformed only when touched lightly. Poor: Deformed even when touched lightly. |
| Thickness Uniformity (Visual Confirmation) | Good | Good | Good: Almost no visible line (thin portion or crack). Not so good: Line is visible, but it does not affect the feel of touch. Poor: Large line nearly causing crack, and feels clearly thin when touching it. |
| Cut Surface Condition (Visual Confirmation) | Good | Good | Good: No visible cut in fiber. Not so good: Some visible cuts in fiber, but they do not affect the shape of bloomed fiber material. Poor: Cut surface is clearly visible. |

It is understood from Table 4 that the bloomed tow according to Working Example 2 has substantially equivalent properties to those of the bloomed tow according to Comparative Example 3. That is, in Working Example 2, the bloomed tow realizes an extremely small basis weight while having substantially equivalent properties to those of the conventional bloomed tow.

Variations

Although a preferred embodiment of the present invention has been described above, the above-described configuration can be modified, for example, as described below.

Figure 5:
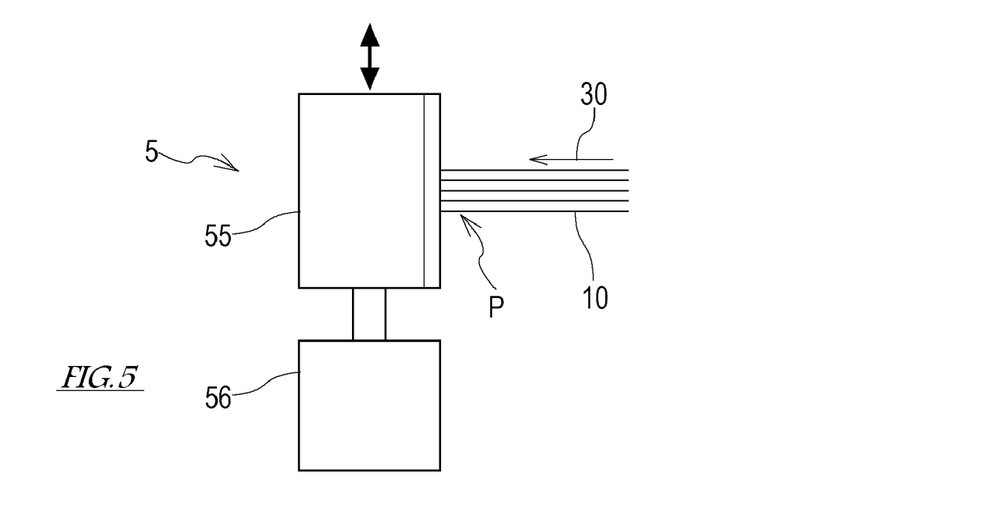
FIG. 5 is a side view showing a variation of the cutting device.

In the above-described embodiment, for example, the disc cutter 51 driven by the driver 52 to rotate is used as the cutting device 5. Accordingly, stable cutting force can be continuously applied to the continuous tow 10. However, the cutting device 5 is not limited to the disc cutter 51. For example, as shown in FIG. 5, a cutter 55 driven by a driver 56 to move in a reciprocating manner can be used as the cutting device 5. Moreover, the cutting device 5 is not limited to a movable cutting tool. Alternatively, for example, a cutting tool whose position relative to the feeding path 30 is fixed can be used as the cutting device 5.

Figure 6:
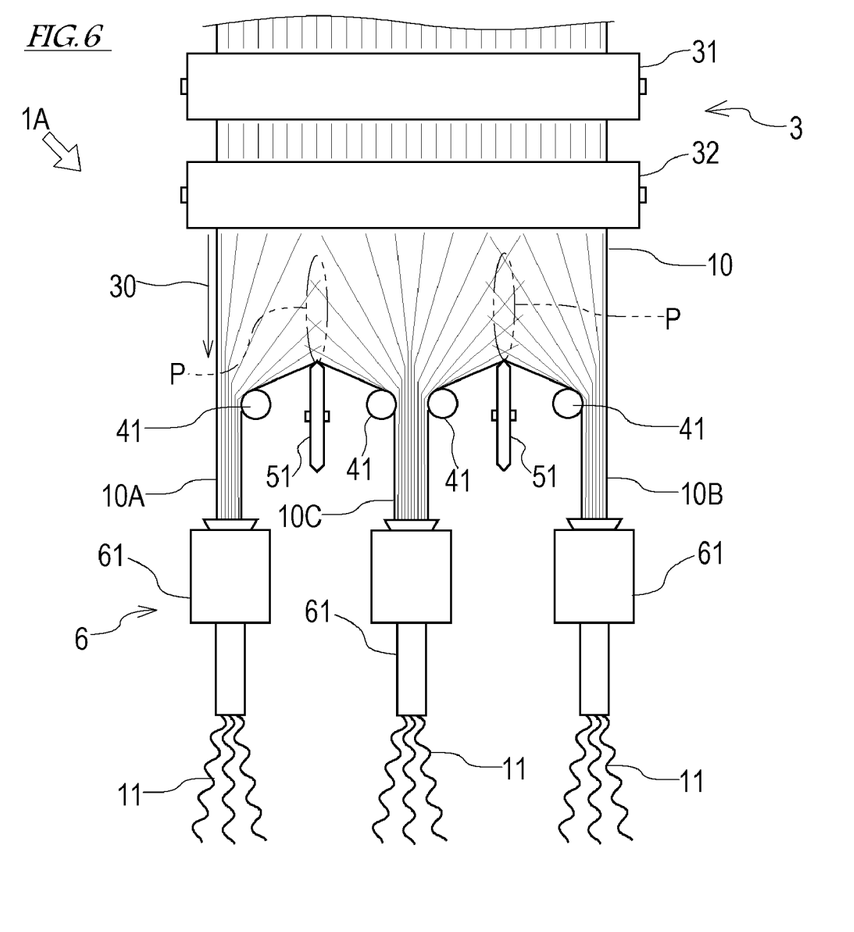
FIG. 6 is a plan view of a part of the bloomed fiber material manufacturing apparatus, which part is positioned following the primary blooming device, according to a first variation in a case where a tow is divided into three divided tows.
Figure 7:
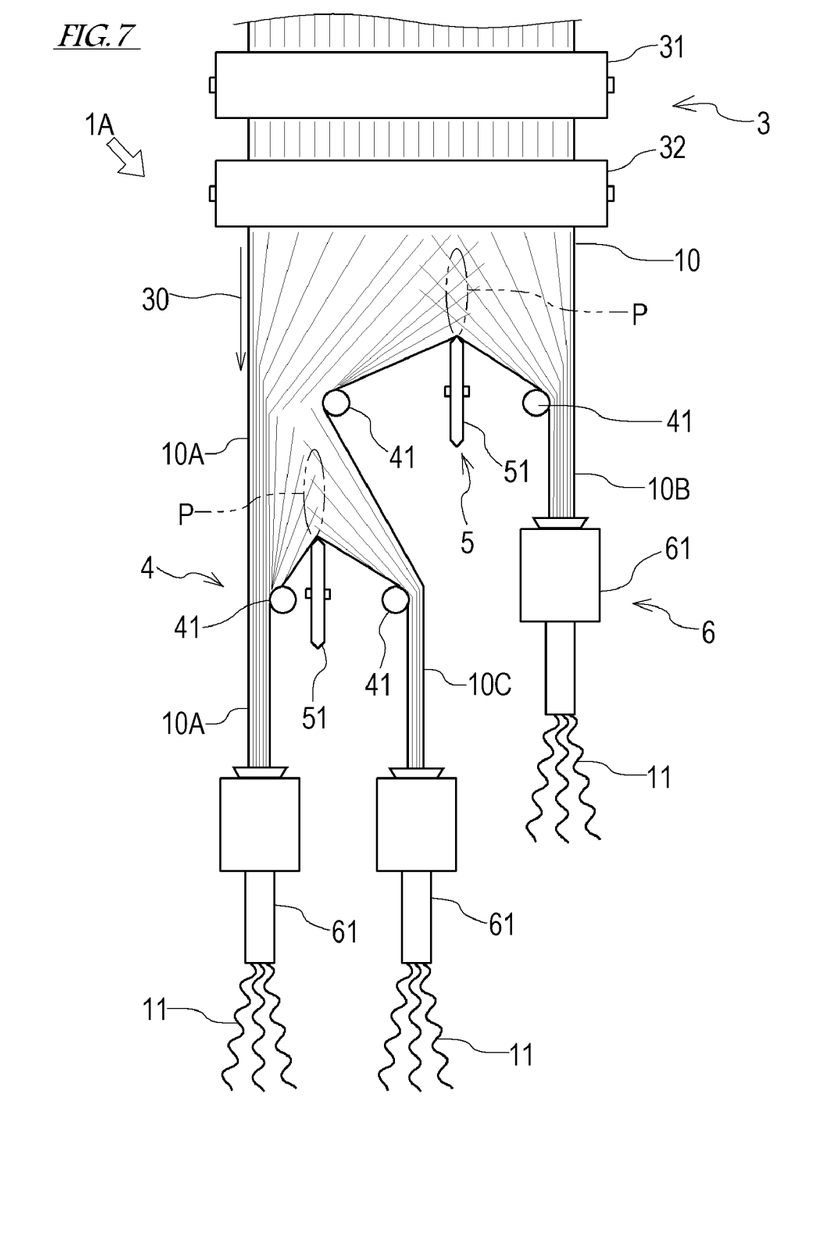
FIG. 7 is a plan view of a part of the bloomed fiber material manufacturing apparatus, which part is positioned following the primary blooming device, according to a second variation in a case where a tow is divided into three divided tows.

Further, in the above-described embodiment, for example, a single tow 10 is divided into two tows. However, as an alternative, a single tow 10 may be divided into three or more tows. For example, as shown in FIG. 6, a single tow 10 may be divided into three divided tows 10A, 10B, and 10C. In this case, four guide bars 41 are used as the dividing device 4 for dividing the single tow 10 into three divided tows 10A, 10B, and 10C. Then, in order to cut each parting P between adjoining divided tows, two disc cutters 51 are used as the cutting device 5. In a bloomed fiber material manufacturing apparatus 1A with this configuration, the preliminary blooming device 2 and the primary blooming device 3 are provided for the single tow 10, and the secondary blooming device 6 is provided for the three divided tows 10A, 10B, and 10C. It should be noted that, in the example shown in FIG. 6, the single tow 10 is divided into the three divided tows 10A, 10B, and 10C at substantially the same positions on the feeding path 30. However, as an alternative, as shown in FIG. 7, the single tow 10 may be first divided into two divided tows 10A and 10B, and thereafter, between this first dividing position and the secondary blooming device, the divided tow 10A may be divided into two divided tows 10A and 10C on the feeding path 30.

Still further, in the above-described embodiment, for example, the dividing device 4 is formed by the two guide bars 41. This configuration is advantageous since the dividing device 4 can be formed at low cost and the maintenance of the dividing device 4 can be readily performed. However, the dividing device 4 is not limited to the guide bars 41. The dividing device 4 may be configured in any form, so long as the dividing device 4 can divide a tow 10 into a plurality of divided tows 10A and 10B and guide the movement of the divided tows 10A and 10B, such that the divided tows 10A and 10B are separated apart from each other in the width direction of the tow 10. For example, at least two rotator-like guide members that are disposed such that they are spaced apart from each other in the width direction of the tow 10 can be used as the dividing device 4. In this case, the divided tows 10A and 10B move in contact with the periphery of the rotator-like guide members. This makes it possible to reduce the friction between the divided tows 10A and 10B and the guide members. Alternatively, for example, at least two cylindrical guide members that are disposed such that they are spaced apart from each other in the width direction of the tow 10 can be used as the dividing device 4. In this case, the divided tows 10A and 10B are inserted through the cylindrical guide members. Further alternatively, for example, at least one block on which a plurality of grooves or passages for allowing the divided tows 10A and 10B to pass through are formed can be used as the dividing device 4.

REFERENCE SIGNS LIST 1 bloomed fiber material manufacturing apparatus
10 tow
11 bloomed tow (bloomed fiber material)
2 preliminary blooming device
21, 22 banding jet
3 primary blooming device
31, 32 pair of blooming rollers
4 dividing device
41 guide bar (guide member)
5 cutting device
51 disc cutter
52 driver
6 secondary blooming device
61 blooming jet
30 feeding path

The invention claimed is:
1. A method of manufacturing a bloomed fiber material, the method comprising:
spreading a crimped tow in a width direction of the tow;
performing primary blooming to bloom the tow that has been spread in the width direction;

dividing the tow that has undergone the primary blooming into at least two divided tows;
cutting a parting between the divided tows; and
performing secondary blooming to bloom the divided tows.

2. The method of manufacturing a bloomed fiber material according to claim 1, wherein
performing the secondary blooming includes:
separating filaments of each of the divided tows from one another;
forming each of the divided tows into an intended shape; and
reducing tensile strength of each of the divided tows.

3. The method of manufacturing a bloomed fiber material according to claim 1, wherein
performing the secondary blooming includes separating filaments of each of the divided tows from one another by a blooming jet.

4. The method of manufacturing a bloomed fiber material according to claim 1, wherein
performing the primary blooming includes separating filaments of the tow from one another by a pair of blooming rollers.

5. The method of manufacturing a bloomed fiber material according to claim 1, wherein
cutting the parting includes cutting filaments of the parting between the divided tows by a rotating disc cutter.

6. The method of manufacturing a bloomed fiber material according to claim 1, wherein
dividing the tow includes separating the divided tows apart from each other in the width direction by a guide member that guides movement of the divided tows.

7. The method of manufacturing a bloomed fiber material according to claim 2, wherein
cutting the parting includes cutting filaments of the parting between the divided tows by a rotating disc cutter.

8. The method of manufacturing a bloomed fiber material according to claim 3, wherein
cutting the parting includes cutting filaments of the parting between the divided tows by a rotating disc cutter.

9. The method of manufacturing a bloomed fiber material according to claim 4, wherein
cutting the parting includes cutting filaments of the parting between the divided tows by a rotating disc cutter.

10. The method of manufacturing a bloomed fiber material according to claim 2, wherein
dividing the tow includes separating the divided tows apart from each other in the width direction by a guide member that guides movement of the divided tows.

11. The method of manufacturing a bloomed fiber material according to claim 3, wherein
dividing the tow includes separating the divided tows apart from each other in the width direction by a guide member that guides movement of the divided tows.

12. The method of manufacturing a bloomed fiber material according to claim 4, wherein
dividing the tow includes separating the divided tows apart from each other in the width direction by a guide member that guides movement of the divided tows.

13. An apparatus for manufacturing a bloomed fiber material, comprising:
a preliminary blooming device configured to spread a crimped tow in a width direction of the tow;
a primary blooming device configured to perform primary blooming to bloom the tow that has been spread in the width direction;
a dividing device configured to divide the tow that has undergone the primary blooming into at least two divided tows;
a cutting device configured to cut a parting between the divided tows; and
a secondary blooming device configured to perform secondary blooming to bloom the divided tows.

14. The apparatus for manufacturing a bloomed fiber material according to claim 13, wherein
the secondary blooming device includes a blooming jet.

15. The apparatus for manufacturing a bloomed fiber material according to claim 14, wherein
a nozzle of the blooming jet is cylindrical.

16. The apparatus for manufacturing a bloomed fiber material according to claim 13, wherein
the primary blooming device includes a pair of blooming rollers.

17. The apparatus for manufacturing a bloomed fiber material according to claim 13, wherein
the cutting device includes a rotating disc cutter.

18. The apparatus for manufacturing a bloomed fiber material according to claim 13, wherein
the dividing device includes a guide member that guides movement of the divided tows, such that the divided tows are separated apart from each other in the width direction.

19. The apparatus for manufacturing a bloomed fiber material according to claim 14, wherein
the cutting device includes a rotating disc cutter.

20. The apparatus for manufacturing a bloomed fiber material according to claim 15, wherein
the cutting device includes a rotating disc cutter.

* * * * *